United States Patent [19]  [11] Patent Number: 4,885,024
Enomoto et al.  [45] Date of Patent: Dec. 5, 1989

[54] BENZOXAZINYL-TRIAZOLE OXIDES AND USE

[75] Inventors: Masayuki Enomoto, Takarazuka; Eiki Nagano, Tokyo; Toru Haga, Toyonaka; Kouichi Morita, Kasai; Ryo Sato, Tokyo, all of Japan

[73] Assignee: Sumitomo Chemical Co., Ltd., Osaka, Japan

[21] Appl. No.: 234,625

[22] Filed: Aug. 22, 1988

[30] Foreign Application Priority Data

Sep. 1, 1987 [JP]  Japan ................... 62-218607

[51] Int. Cl.$^4$ ................... A01N 43/76; C07D 413/02
[52] U.S. Cl. ........................... 71/92; 544/105
[58] Field of Search ............... 544/105; 71/92

[56] References Cited

U.S. PATENT DOCUMENTS 4,608,080  8/1986  Haga et al. ............... 71/92
4,619,687  10/1986 Haga et al. ............... 71/92
4,640,707  2/1987  Nagano et al. ............ 71/96
4,670,043  6/1987  Nagano et al. ............ 71/92
4,752,325  6/1988  Haga et al. ............... 71/92

Primary Examiner—Richard L. Raymond
Attorney, Agent, or Firm—Birch, Stewart, Kolasch & Birch

[57] ABSTRACT

A compound of the formula:

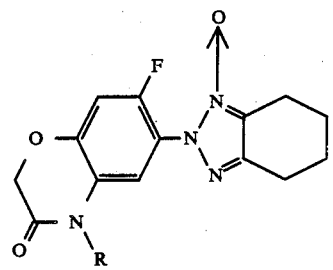

wherein R is a $C_1$–$C_6$ alkyl group, a $C_3$–$C_7$ alkenyl group, a $C_3$–$C_7$ alkynyl gorup, a $C_1$–$C_4$ alkoxy($C_1$–$C_2$) alkyl group, a halo($C_1$–$C_5$)alkyl group, a halo($C_3$–$C_4$)alkenyl group or a halo($C_3$–$C_4$)alkynyl group, which is useful as a herbicide.

21 Claims, No Drawings

BENZOXAZINYL-TRIAZOLE OXIDES AND USE

The present invention relates to benzoxazinyltriazole oxides, their production and use. More particularly, it relates to novel benzoxazinyl-triazole oxides, a process for producing them, and their use as herbicides.

U.S. Pat. No. 4,668,278 discloses some triazole oxides useful as herbicides. Also, U.S. Pat. No. 4,640,707 discloses some oxazines useful as herbicides. However, these known herbicides are not sufficient in herbicidal potency or have poor selectivity between crop plants and weeds. Their herbicidal activity is thus not necessarily satisfactory.

It has now been found that benzoxazinyl-triazole oxides of the formula:

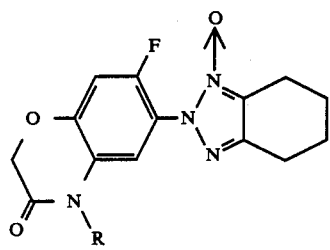

wherein R is a $C_1$-$C_6$ alkyl group, a $C_3$-$C_7$ alkenyl group, a $C_3$-$C_7$ alkynyl group, a $C_1$-$C_4$ alkoxy($C_1$-$C_2$)alkyl group, a halo($C_1$-$C_5$)alkyl group, a halo($C_3$-$C_4$)alkenyl group or a halo($C_3$-$C_4$)alkynyl group show a high herbicidal potency against various weeds with a high selectivity between crop plants and weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, wheat, rice plant, soybean, cotton and sugarbeet. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), etc. Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of the Commelinaceous weeds include asiatic dayflower (*Commelina communis*), etc. Examples of the Cyperaceous weeds include purple nutsedge (*Cyperus rotundus*), etc.

The benzoxazinyl-triazole oxides (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirpus juncoides*) and needle spikerush (*Eleocharis acicularis*), and others such as monochoria (*Monochoria vaginalis*) and arrowhead (*Sagittaria pygmaea*) without producing any phytotoxicity to rice plants on flooding treatment.

Among the benzoxazinyl-triazole oxides (I), preferred are those wherein R is a $C_1$-$C_6$ alkyl group, a $C_3$-$C_4$ alkenyl group or a $C_3$-$C_4$ alkynyl group, particularly those wherein R is a $C_3$-$C_4$ alkynyl group. Typical example of the preferred compounds is 2-(7-fluoro-4-propargyl-2H-1,4-benzoxazin-3(4H)-on-6-yl)-4,5,6,7-tetrahydro-1,2,3-benzotriazole-1-oxide.

The benzoxazinyl-triazole oxides (I) of the invention can be produced by either one of the following procedures:

Procedure (A):

The benzoxazinyl-triazole oxide (I) is prepared by reacting an oxime of the formula:

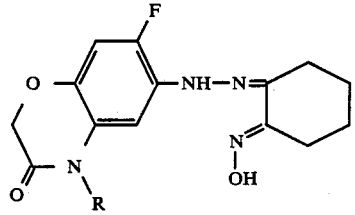

wherein R is as defined above with an oxidizing agent for ring closure. The reaction is usually performed in an inert solvent at a temperature of about 10° to 100° C. for a period of about 1 to 10 hours.

As the oxidizing agent, there may be used mercury oxide, copper sulfate, lead tetra-acetate, etc. Among them, copper sulfate is particularly favorable. The amount of the oxidizing agent is used is from about 1 to 1.5 equivalents to one equivalent of the oxime (II). Examples of the solvent are ethers (e.g. diethyl ether, diisopropyl ether, dioxane, tetrahydrofuran, diethyleneglycol dimethyl ether), tertiary amines (e.g. pyridine), water, etc. These may be used solely or in combination.

After completion of the reaction, the reaction mixture is subjected to ordinary post-treatment such as extraction with an organic solvent and concentration. If desired, any conventional purification procedure such as chromatography or recrystallization may be applied to the product.

According to this procedure, there are obtainable the benzoxazinyl-triazole oxides (I) wherein R is an alkyl group (e.g. methyl, ethyl, propyl, isopropyl, butyl, isobutyl, sec-butyl, pentyl, hexyl), an alkenyl group (e.g. allyl, 2-butenyl, 3-butenyl, 2-methylallyl, 2-methyl-2-butenyl), an alkynyl group (e.g. propargyl, 1-methylpropargyl, 2-butynyl, 1-methyl-2-butynyl), an alkoxyalkyl group (e.g. methoxymethyl, ethoxymethyl, 1-methoxyethyl, 1-ethoxyethyl, 2-methoxyethyl, 2-ethoxyethyl), a haloalkyl group (e.g. trifluoromethyl, difluoromethyl, 1,1,2,2-tetrafluoroethyl, 2-fluoroethyl, 1,1,2,2-tetrafluoropropyl), a haloalkenyl group (e.g. 2-chloroallyl, 3,3-dichloroallyl, 2,3,3-trichloroallyl), a haloalkynyl group (e.g. 3-chloropropargyl, 3-bromopropargyl), etc.

Procedure (B):

The benzoxazinyl-triazole oxide (I) is prepared by reacting a triazole oxide of the formula:

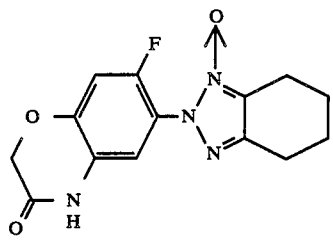
(III)

with an R-introducing agent of the formula:

R—Y  (IV)

wherein R is as defined above and Y is the residue of a strong acid excluding a hydrogen atom therefrom such as a halogen atom (e.g. chlorine, bromine, iodine) or a sulfonyl group (e.g. methanesulfonyl, p-toluenesulfonyl). The reaction is usually effected in the presence of an acid-binding agent in an inert solvent at a temperature of about 0° to 60° C. for a period of about 0.5 to 3 hours.

Normally, the R-introducing agent (IV) and the acid-binding agent are used respectively in amounts of about 1.0 to 1.2 equivalents and of about 1.0 to 1.2 equivalents to one equivalent of the triazole oxide (III). As the acid-binding agent, there may be used a base such as sodium hydroxide, potassium hydroxide, sodium carbonate, potassium carbonate or sodium hydride. Examples of the solvent are aromatic hydrocarbons (e.g. benzene, toluene, xylene), ethers (e.g. diethyl ether, diisopropyl ether, dioxane, tetrahydrofuran, diethyleneglycol dimethyl ether), acid amides (e.g. formamide, N,N-dimethylformamide, acetamide), sulfurous compounds (e.g. dimethylsulfoxide, sulphorane), aqueous ammonia, etc. These may be used solely or in combination.

After completion of the reaction, the reaction mixture is subjected to ordinary post-treatment. For instance, the reaction mixture is poured into water, and the precipitated crystals are collected by filtration. Alternatively, the reaction mixture is shaken in combination with water and a water-immiscible organic solvent for extraction, and the extract is concentrated. If desired, any conventional purification procedure such as chromatography or recrystallization may be applied to the resulting product.

According to this procedure, there are obtainable the benzoxazinyl-triazole oxides (I) wherein R is an alkyl group (e.g. methyl, ethyl, propyl, isopropyl, butyl, isobutyl, sec-butyl, pentyl, hexyl), an alkenyl group (e.g. allyl, 1-methylallyl, 2-butenyl, 1-methyl-2-butenyl, 3-methyl-2-butenyl, 1,3-dimethyl-2-butenyl, 2,3-dimethyl-2-butenyl, 1,2,3-trimethyl-2-butenyl), an alkynyl group (e.g. propargyl, 1-methylpropargyl, 2-butynyl, 1-methyl-2-butynyl), an alkoxyalkyl group (e.g. methoxymethyl, ethoxymethyl, propoxymethyl, butoxymethyl, 1-methoxyethyl, 1-ethoxyethyl, 2-methoxyethyl, 2-ethoxyethyl, 2-propoxyethyl), a haloalkyl group (e.g. 2-fluoroethyl, 1,1,2,2-tetrafluoroethyl, trifluoromethyl, 2-chloroethyl), a haloalkenyl group (e.g. 2-chloroallyl, 3,3-dichloroallyl, 2,3,3-trichloroallyl), a haloalkynyl group (e.g. 3-chloropropargyl, 3-bromopropargyl), etc.

Some typical embodiments for production of the benzoxazinyl-triazole oxides (I) are illustratively shown in the following Examples.

EXAMPLE 1

Preparation of 2-(7-fluoro-4-propargyl-2H-1,4-benzoxazin-3(4H)-on-6-yl)-4,5,6,7-tetrahydro-1,2,3-benzotriazole-1-oxide (Compound No. 1)

To a solution of 2-[2-(7-fluoro-4-propargyl-2H-1,4-benzoxazin-3(4H)-on-6-yl)hydrazino]cyclohexanone oxime (0.4 g) in tetrahydrofuran (6 ml), 15% aqueous pyridine (7 g) was added, and a solution of copper sulfate (0.7 g) in water (1.5 ml) was added thereto, followed by heating at 80° C. for 2 hours. The reaction mixture was allowed to cool, combined with water and extracted with ethyl acetate. The organic layer was washed with 10% aqueous copper sulfate solution, dried and concentrated. The residue was purified by silica gel column chromatography using ethyl acetate as an eluent to give Compound No. 1 (0.2 g). m.p., 186°–187° C.

EXAMPLE 2

Preparation of 2-(7-fluoro-4-ethyl-2H-1,4-benzoxazin-3(4H)-on-6-yl)-4,5,6,7-tetrahydro-1,2,3-benzotriazole-1-oxide (Compound No. 2)

To a solution of 2-(7-fluoro-2H-1,4-benzoxazin-3(4H)-on-6-yl)-4,5,6,7-tetrahydro-1,2,3-benzotriazole-1-oxide (0.5 g) in dimethylformamide (5 ml), sodium hydride (0.1 g) and then ethyl iodide (0.3 g) were added, followed by heating at 40° C. for 2 hours. The reaction mixture was poured into water, and the precipitated crystals were collected by filtration, dried and recrystallized from a mixture of acetonitrile and isopropanol (1:10) to give Compound No. 2 (0.4 g). m.p., 143°–144° C.

In the same manner as above, the compounds (I) as shown in Table 1 were obtained.

TABLE 1

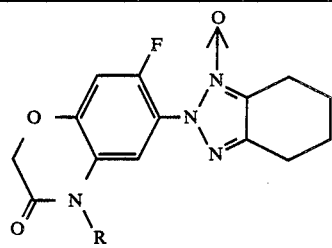
(I)

| Compound No. | R | Physical property |
|---|---|---|
| 1 | $CH_2C{\equiv}CH$ | m.p., 186–187° C. |
| 2 | $C_2H_5$ | m.p., 143–144° C. |
| 3 | $CH_2OCH_3$ | $n_D^{26.3}$ 1.5682 |
| 4 | $CH_2CH_2F$ | m.p., 151–153° C. |
| 5 | $CH_2CH{=}CH_2$ | m.p., 178–179° C. |
| 6 | $CH_2CH_2CH_3$ | m.p., 152–154° C. |
| 7 | $CH(CH_3)C{\equiv}CH$ | m.p., 198–199° C. |
| 8 | $CH_3$ | m.p., 169–170° C. |
| 9 | $CH_2OC_2H_5$ | resinous |

The oxime (II) and the triazole oxide (III) used as the starting materials in the above procedures may be produced according to the following scheme:

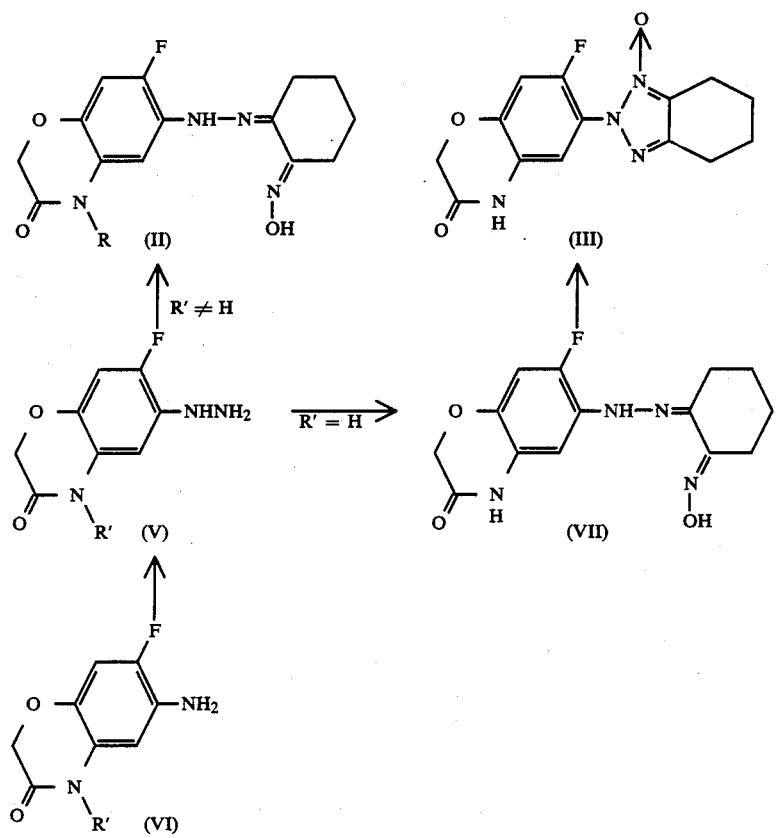

wherein R' is a hydrogen atom, a $C_1$-$C_6$ alkyl group, a $C_3$-$C_7$ alkenyl group, a $C_3$-$C_7$ alkynyl group, a $C_1$-$C_4$ alkoxy($C_1$-$C_2$)alkyl group, a halo($C_1$-$C_5$)alkyl group, a halo($C_3$-$C_4$)alkenyl group or a halo($C_3$-$C_4$)alkynyl group and R is as defined above.

The reaction at each step in the foregoing scheme will be hereinafter explained in detail.

Procedure (1):

The oxime (II) or (VII) is obtained by reacting the hydrazine (V) with an enaminoxime of the formula:

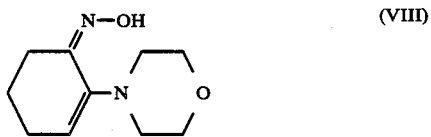

(VIII)

in the presence of a catalytic amount of an acid in an inert solvent, normally at a temperature of about 10° to 100° C. for a period of about 0.5 to 10 hours.

In the above reaction, the enaminoxime (VIII) is usually employed in an amount of about 1 to 1.05 equivalents to one equivalent of the hydrazine (V). As the acid, there may be used acetic acid, p-toluenesulfonic acid or the like. Examples of the solvent are alcohols (e.g. methanol, ethanol, cellosolve), ethers (e.g. dioxane, tetrahydrofuran), etc.

After completion of the reaction, the reaction mixture is subjected to ordinary post-treatment. For instance, the reaction mixture is poured into water, and the precipitated crystals are collected by filtration. Alternatively, the reaction mixture is admixed with water and extracted with an organic solvent, followed by concentration of the extract. When desired, any conventional purification procedure such as chromatography or recrystallization may be applied to the resulting product.

A typical example for production of the oxime (II) or (VII) is illustratively shown in the following Example.

EXAMPLE 3

To a solution of 7-fluoro-4-propargyl-2H-1,4-benzoxazin-3(4H)-on-6-ylhydrazine (2.5 g) and enaminoxime (2.5 g) in ethanol (50 g), acetic acid (0.1 g) was added, and the resultant mixture was heated under reflux for 3 hours. After completion of the reaction, water was added to the reaction mixture, and the precipitated crystals were collected by filtration and washed with ether to give 2-[2-(7-fluoro-4-propargyl-2H-1,4-benzoxazin-3(4H)-on-6-yl)hydrazino]cyclohexanone oxime (4.0 g).

In the same manner as above, the compounds as shown in Table 2 were obtained:

TABLE 2

(II) or (VII)

| R' | Physical property |
|---|---|
| H | m.p., 252–253° C. (decomp.) |
| $C_2H_5$ | m.p., 218–219° C. (decomp.) |

TABLE 2-continued (II) or (VII)

structure: 4-fluoro-phenyl with O-CH2-CH2-C(=O)-N(R')- forming benzoxazinone ring, and -NH-N= linked to cyclohexanone oxime (=N-OH)

| R' | Physical property |
|---|---|
| CH$_2$C≡CH | m.p., 240–241° C. (decomp.) |
| CH$_2$CH=CH$_2$ | m.p., 209–210° C. (decomp.) |
| n-C$_3$H$_7$ | resinous |

Procedure (2):
The triazole oxide (III) is obtainable from the oxime (VII) in the same manner as in Procedure (A).

A typical example for production of the triazole oxide (III) is set forth below.

EXAMPLE 4

To a solution of 2-[2-(7-fluoro-2H-1,4-benzoxazin-3(4H)-on-6-yl)hydrazino]cyclohexanone oxime (3.0 g) in tetrahydrofuran (100 ml), 15% aqueous pyridine (60 g) was added, and a solution of copper sulfate (6 g) in water (10 ml) was added thereto, followed by heating at 80° C. for 2 hours. After completion of the reaction, the reaction mixture was poured into water and extracted with ethyl acetate. The extract was washed with 10% aqueous copper sulfate solution, dried and concentrated. The residue was purified by silica gel column chromatography using ethyl acetate as an eluent to give 2-(7-fluoro-2H-1,4-benzoxazin-3(4H)-on-6-yl)-4,5,6,7-tetrahydro-1,2,3-benzotriazole-1-oxide. m.p., 219°–221° C.

$^1$H-NMR (δ, CDCl$_3$): 1.7–2.1 (br, 4H), 2.5–3.0 (br, 4H), 4.62 (s, 2H), 6.68 (d, 1H, J=8 Hz), 6.83 (d, 1H, J=11 Hz), 10–11 (br, 1H).

Procedure (3):
The hydrazine (V) is prepared from the amine (VI) according to the method as described in J. Chem. Soc., (c), 1970, 2106. Namely, the amine (VI) is diazotiated by reacting with an alkali metal nitrite in an amount of 1.0 to 1.2 equivalents to the former in hydrochloric acid or sulfuric acid at a temperature of about −5° to 5° C. for a period of about 0.5 to 24 hours. The resultant diazonium solution is then reacted with anhydrous stannous chloride in an amount of about 2 to 3 equivalents to the amine (VI) at a temperature of about −20° to 50° C. for a period of about 0.5 to 3 hours. The reaction mixture is neutralized at a temperature lower than about 10° C. and extracted with an organic solvent. The extract is dried and concentrated to give the hydrazine (V). When desired, the product may be purified by recrystallization or column chromatography.

A typical example for production of the hydrazine (V) is illustratively shown in the following Example.

EXAMPLE 5

A suspension of 6-amino-7-fluoro-4-propargyl-2H-1,4-benzoxazin-3(4H)-one (13.0 g) in conc. hydrochloric acid (70 g) was cooled to 0° to 5° C., and a saturated solution of sodium nitrite (5.1 g) was dropwise added thereto at 0° to 5° C., followed by stirring for 2 hours. The resultant mixture was cooled to −30° C., and a solution of anhydrous stannous chloride (28.1 g) in conc. hydrochloric acid (30 g) was added thereto at once, followed by stirring at 0° to 5° C. for 3 hours. Celite (50 g) was added to the reaction mixture, which was neutralized with 10% aqueous sodium hydroxide solution below 10° C. The resulting mixture was filtered, and the filtrate was extracted with ethyl acetate. The extract was washed with water, dried and concentrated to give 7-fluoro-4-propargyl-2H-1,4-benzoxazin-3(4H)-on-6-ylhydrazine (8.2 g).

In the same manner as above, the compounds as shown in Table 3 were obtained.

TABLE 3 benzoxazinone with F and NHNH$_2$ substituents, N-R'

| R' | Physical property |
|---|---|
| CH$_2$C≡CH | m.p., 82–84° C. (decomp.) |
| | $^1$H—NMR (δ, CDCl$_3$ + d$_6$-DMSO): 3.1–3.2 (t, 1H, J = 3 Hz), 3.7–4.2 (br, 2H), 4.5 (s, 2H), 4.6 (d, 2H, J = 3 Hz), 6.2–6.7 (br, 1H), 6.75 (d, 1H, J = 12 Hz), 7.05 (d, 1H, J = 8 Hz) |
| H | m.p., 92–94° C. (decomp.) |
| | $^1$H—NMR (δ, d$_6$-DMSO): 3.2–4.0 (br, 3H), 4.38 (s, 2H), 6.55 (d, 1H, J = 12 Hz), 6.77 (d, 1H, J = 8 Hz), 10–11 (br, 1H) |
| C$_2$H$_5$ | m.p., 79–82° C. (decomp.) |
| CH$_2$CH=CH$_2$ | m.p., 69–71° C. (decomp) |

The amine (VI) can be produced by the method as disclosed in U.S. Pat. No. 4,640,707.

For the practical usage of the benzoxazinyltriazole oxide (I), it is usually formulated with conventional solid or liquid carriers or diluents as well as surface active agents or auxiliary agents into conventional preparation forms such as emulsifiable concentrates, wettable powders, suspensions and granules. The content of the benzoxazinyl-triazole oxide (I) as the active ingredient in such preparation forms is normally within a range of about 0.05 to 90% by weight, preferably of about 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent usable for emulsification, dispersing or spreading may be of any type, for instance, either anionic or non-ionic. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc.

Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one as shown in Table 1.

FORMULATION EXAMPLE 1

Fifty parts of Compound No. 1, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of any one of Compound Nos. 1 to 9, 14 parts of polyoxyethylenestyrylphenyl ether, 6 parts of calcium dodecylbenzenesulfonate, 30 parts of xylene and 40 parts of cyclohexanone are well mixed to obtain an emulsifiable concentrate.

FORMULATION EXAMPLE 3

Two parts of Compound No. 1, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 1, 3 parts of polyoxyethylene sorbitan monooleate, 3 parts of carboxymethyl cellulose and 69 parts of water are mixed and pulverized until the particle size becomes less than 5 microns to obtain a suspension.

The benzoxazinyl-triazole oxide (I) thus formulated in any suitable preparation form is useful for pre-emergence or post-emergence control of undesired weeds by soil or foliar treatment as well as flood fallowing treatment. These treatments include application to the soil surface prior to or after transplanting, incorporation into the soil, etc. The foliar treatment may be effected by spraying the herbicidal composition containing the benzoxazinyl-triazole oxide (I) over the top of plants. It may also be applied directly to the weeds if care is taken to keep the chemical off the crop foliage.

The benzoxazinyl-triazole oxide (I) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. Furthermore, it may be used as a herbicide applicable to agricultural plowed fields as well as paddy fields. It is also useful as a herbicide to be employed for orchards, pasture land, lawns, forests, non-agricultural fields, etc.

The dosage of the benzoxazinyl-triazole oxide (I) may vary depending on the prevailing weather conditions, the formulation used, the prevailing season, the mode of application, the soil involved, the crop and weed species, etc. Generally, however, the dosage is from about 0.02 to 100 grams, preferably from about 0.05 to 50 grams, of the active ingredient per are. The herbicidal composition of the invention formulated in the form of an emulsifiable concentrate, a wettable powder or a suspension may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the benzoxazinyl-triazole oxide (I) as a herbicide will be illustratively shown in the following Examples wherein the phytotoxicity to crop plants and the herbicidal activity on weeds were observed visually as to the degree of germination as well as the growth inhibition and rated with an index 0, 1, 2, 3, 4, 5, 6, 7, 8, 9 and 10, The compounds as shown in Table 4 were used for comparison.

TABLE 4

| Compound No. | Structure | Remarks |
| --- | --- | --- |
| A | [Cl-phenyl-N-triazole oxide fused cyclohexane] | U.S. Pat. No. 4,668,278 |
| B | [Br-phenyl-N-triazole oxide fused cyclohexane] | U.S. Pat. No. 4,668,278 |
| C | [F,Cl-phenyl-N-triazole oxide fused cyclohexane] | U.S. Pat. No. 4,668,278 |
| D | [F-phenyl-N-imide fused cyclohexene structure] | U.S. Pat. No. 4,640,707 |

TEST EXAMPLE 1

Cylindrical plastic pots (diameter, 10 cm; height, 10 cm) were filled with upland field soil, and the seeds of Japanese millet, oats, radish and velvetleaf were sowed therein and covered with soil and cultivated in a greenhouse for 10 days. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 5.

TABLE 5

| Compound No. | Dosage (g/are) | Herbicidal activity | | | |
|---|---|---|---|---|---|
| | | Japanese millet | Oats | Radish | Velvetleaf |
| 1 | 10 | 10 | 10 | 10 | 10 |
| 2 | 10 | 10 | 10 | 10 | 10 |
| 3 | 10 | 10 | 10 | 10 | 10 |
| 4 | 10 | 10 | 10 | 10 | 10 |
| 5 | 10 | 10 | 10 | 10 | 10 |
| 6 | 10 | 10 | 10 | 10 | 10 |
| 7 | 10 | 10 | 10 | 10 | 10 |
| 8 | 10 | 10 | 10 | 10 | 10 |
| 9 | 10 | 10 | 10 | 10 | 10 |

TEST EXAMPLE 2

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 6.

TABLE 6

| Compound No. | Dosage (g/are) | Herbicidal activity | | | |
|---|---|---|---|---|---|
| | | Japanese millet | Oats | Tall morningglory | Velvetleaf |
| 1 | 5 | 10 | 10 | 10 | 10 |
| 2 | 5 | 10 | 10 | 10 | 10 |
| 3 | 5 | 10 | 10 | 10 | 10 |
| 4 | 5 | 10 | 10 | 10 | 10 |
| 5 | 5 | 10 | 10 | 10 | 10 |
| 6 | 5 | 10 | 10 | 10 | 10 |
| 7 | 5 | 10 | 10 | 10 | 10 |
| 8 | 5 | 10 | 10 | 10 | 10 |
| 9 | 5 | 10 | 10 | 10 | 10 |
| A | 5 | 0 | 0 | 0 | 3 |
| B | 5 | 0 | 0 | 0 | 1 |

TEST EXAMPLE 3

Cylindrical plastic pots (diameter, 10 cm; height, 10 cm) were filled with upland field soil, and the seeds of Japanese millet and oats were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 7.

TABLE 7

| Compound No. | Dosage (g/are) | Herbicidal activity | |
|---|---|---|---|
| | | Japanese millet | Oats |
| 1 | 5 | 10 | 10 |
| 2 | 5 | 10 | 10 |
| 3 | 5 | 10 | 10 |
| 4 | 5 | 10 | 10 |
| 5 | 5 | 10 | 10 |
| 6 | 5 | 10 | 10 |
| 7 | 5 | 10 | 10 |
| 8 | 5 | 10 | 10 |
| 9 | 5 | 10 | 10 |
| A | 5 | — | 5 |
| B | 5 | 6 | 6 |

TEST EXAMPLE 4

Cylindrical plastic pots (diameter, 8 cm; height, 12 cm) were filled with paddy field soil, and the seeds of barnyardgrass (*Echinochloa oryzicola*) and hardstem bulrush were sowed in 1 to 2 cm depth. Water was poured therein to make a flooded condition, and tubers of arrowhead were transplanted therein in 1 to 2 cm depth, and the test plants were grown in a greenhouse. Six days (at that time weeds began to germinate) thereafter, a designated amount of the test compound formulated in an emulsifiable concentrate as in Formulation Example 2 and diluted with water (5 ml) was applied to the pots by perfusion. The test plants were grown for additional 20 days in the greenhouse, and the herbicidal activity was examined. The results are shown in Table 8.

TABLE 8

| Compound No. | Dosage (g/are) | Herbicidal activity | | |
|---|---|---|---|---|
| | | Barnyardgrass | Hardstem bulrush | Arrowhead |
| 1 | 2.5 | 10 | 10 | 10 |
| 2 | 2.5 | 10 | 10 | 10 |
| 3 | 2.5 | 10 | 10 | 10 |
| 4 | 2.5 | 10 | 10 | 10 |
| 5 | 2.5 | 10 | 10 | 10 |
| 6 | 2.5 | 10 | 10 | 10 |
| 7 | 2.5 | 10 | 10 | 10 |
| 8 | 2.5 | 10 | 10 | 10 |
| 9 | 2.5 | 10 | 10 | 10 |
| A | 2.5 | 2 | 1 | 2 |
| B | 2.5 | 2 | 1 | 1 |

TEST EXAMPLE 5

Vats (33 cm × 23 cm × 11 cm) were filled with upland field soil, and the seeds of tall morningglory, common cocklebur, sicklepod, barnyardgrass (*Echinochloa crusgalli*), johnsongrass, green foxtail and velvetleaf were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 9.

TABLE 9

| Compound No. | Dosage (g/are) | Herbicidal activity | | | | | | |
|---|---|---|---|---|---|---|---|---|
| | | Tall morningglory | Common cocklebur | Sicklepod | Barnyardgrass | Johnsongrass | Green foxtail | Velvetleaf |
| 1 | 2.5 | 10 | 10 | 10 | 10 | 10 | 10 | 10 |

TABLE 9-continued

| Compound No. | Dosage (g/are) | Tall morning-glory | Common cocklebur | Sicklepod | Barn-yard-grass | Johnson-grass | Green foxtail | Velvet-leaf |
|---|---|---|---|---|---|---|---|---|
| | 0.63 | 8 | 8 | 6 | 4 | 10 | 10 | 10 |
| 2 | 2.5 | 10 | 9 | 10 | 10 | 10 | 10 | 10 |
| 7 | 2.5 | 10 | 10 | 10 | 10 | 10 | 10 | 10 |
| A | 2.5 | 0 | 0 | 0 | 0 | 0 | 5 | — |
| B | 2.5 | 0 | 0 | 0 | 0 | 0 | 0 | — |
| C | 2.5 | 0 | 4 | 6 | 2 | 3 | 6 | 8 |
| D | 2.5 | 7 | 3 | 10 | 8 | 9 | 10 | 10 |
| | 0.63 | 1 | 0 | 7 | 4 | 4 | 9 | 10 |

TEST EXAMPLE 6

Vats (33 cm×23 cm×11 cm) were filled with upland field soil, and the seeds of corn, tall morningglory, common cocklebur and black nightshade were sowed therein and cultivated for 18 days in a greenhouse. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 10.

TABLE 10

| Compound No. | Dosage (g/are) | Corn | Tall morning-glory | Common cocklebur | Black night-shade |
|---|---|---|---|---|---|
| 1 | 0.08 | 2 | 10 | 7 | 10 |
| 2 | 0.32 | 2 | 10 | 4 | 8 |
| | 0.08 | 1 | 8 | — | 5 |
| 3 | 0.32 | 3 | 10 | 4 | 8 |
| | 0.08 | 2 | 10 | — | 4 |
| A | 0.08 | 0 | 0 | 0 | 0 |
| B | 0.08 | 0 | 0 | 0 | 0 |

TEST EXAMPLE 7

Vats (33 cm×23 cm×11 cm) were filled with upland field soil, and the seeds of soybean, velvetleaf, sicklepod, barnyardgrass (Echinochloa crus-galli) and green foxtail were sowed in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 11.

TABLE 11

| Compound No. | Dosage (g/are) | Soy-bean | Velvetleaf | Sickle-pod | Barn-yard-grass | Black night-shade |
|---|---|---|---|---|---|---|
| 2 | 1.25 | 0 | 10 | 8 | 7 | 9 |
| A | 1.25 | 0 | 0 | 0 | 0 | 1 |
| B | 1.25 | 0 | 0 | 0 | 0 | 0 |

TEST EXAMPLE 8

Vats (33 cm×23 cm×11 cm) were filled with upland field soil, and the seeds of soybean, velvetleaf, green foxtail and johnsongrass were sowed in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 12.

TABLE 12

| Compound No. | Dosage (g/are) | Soybean | Velvet-leaf | Green foxtail | Johnson-grass |
|---|---|---|---|---|---|
| 3 | 1.25 | 0 | 10 | 8 | 7 |
| A | 1.25 | 0 | 0 | 1 | 0 |
| B | 1.25 | 0 | 0 | 0 | 0 |

What is claimed is:
1. A compound of the formula:

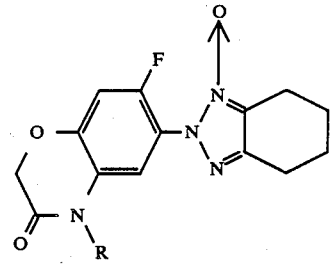

wherein R is a $C_1$-$C_6$ alkyl group, a $C_3$-$C_7$ alkenyl group, a $C_3$-$C_7$ alkynyl group, a $C_1$-$C_4$ alkoxy($C_1$-$C_2$)alkyl group, a halo($C_1$-$C_5$)alkyl group, a halo($C_3$-$C_4$)alkenyl group or a halo($C_3$-$C_4$)alkynyl group.

2. The compound according to claim 1, wherein R is a $C_1$-$C_6$ alkyl group, a $C_3$-$C_4$ alkenyl group or a $C_3$-$C_4$ alkynyl group.

3. The compound according to claim 1, wherein R is a $C_3$-$C_4$ alkynyl group.

4. The compound according to claim 1, wherein R is a propargyl group.

5. The compound according to claim 1, wherein R is $C_2H_5$.

6. The compound according to claim 1, wherein R is $CH_2OCH_3$.

7. The compound according to claim 1, wherein R is $CH_2CH_2F$.

8. The compound according to claim 1, wherein R is CH₂CH=CH₂.

9. The compound according to claim 1, wherein R is CH₂CH₂CH₃.

10. The compound according to claim 1, wherein R is CH(CH₃)C≡CH.

11. The compound according to claim 1, wherein R is CH₃.

12. The compound according to claim 1, wherein R is CH₂OC₂H₅.

13. A compound of the formula:

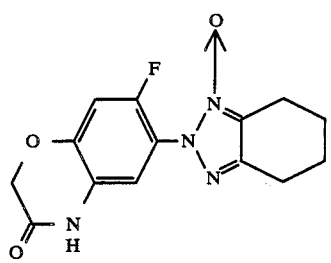

14. A herbicidal composition which comprises as an active ingredient a herbicidally effective amount of the compound according to claim 1, and an inert carrier or diluent.

15. A herbicidal composition which comprises as an active ingredient a herbicidally effective amount of the compound according to claim 2, and an inert carrier or diluent.

16. A herbicidal composition which comprises as an active ingredient a herbicidally effective amount of the compound according to claim 3, and an inert carrier or diluent.

17. A herbicdal composition which comprises as an active ingredient a herbicidally effective amount of the compound according to claim 4, and an inert carrier or diluent.

18. A method for controlling the growth of undesired weeds, which comprises applying a herbicidally effective amount of the compound according to claim 1 and an inert carrier or diluent to the area where the undesired weeds grow or will grow.

19. A method for controlling the growth of undesired weeds, which comprises applying a herbicidally effective amount of the compound according to claim 2 and an inert carrier or diluent to the area where the undesired weeds grow or will grow.

20. A method for controlling the growth of undesired weeds, which comprises applying a herbicidally effective amount of the compound according to claim 3 and an inert carrier or diluent to the area where the undesired weeds grow or will grow.

21. A method for controlling the growth of undesired weeds, which comprises applying a herbicidally effective amount of the compound according to claim 4 and an inert carrier or diluent to the area where the undesired weeds grow or will grow.

* * * * *